United States Patent
Taylor-Hayward et al.

(10) Patent No.: US 7,986,406 B2
(45) Date of Patent: Jul. 26, 2011

(54) METHOD AND APPARATUS FOR SPECTROSCOPIC ANALYSIS

(75) Inventors: Ian Kevin Taylor-Hayward, Hedon (GB); Alasdiar Iain Thomson, Hull (GB)

(73) Assignee: BP Chemicals Limited, Sunbury on Thames (GB)

( * ) Notice: Subject to any disclaimer, the term of this patent is extended or adjusted under 35 U.S.C. 154(b) by 449 days.

(21) Appl. No.: 12/084,033

(22) PCT Filed: Nov. 17, 2006

(86) PCT No.: PCT/GB2006/004295
§ 371 (c)(1),
(2), (4) Date: Apr. 24, 2008

(87) PCT Pub. No.: WO2007/060398
PCT Pub. Date: May 31, 2007

(65) Prior Publication Data
US 2009/0153854 A1    Jun. 18, 2009

(30) Foreign Application Priority Data

Nov. 22, 2005 (EP) .................................. 05257186

(51) Int. Cl.
*G01N 1/10*  (2006.01)
(52) U.S. Cl. ..................................................... 356/246
(58) Field of Classification Search ........... 356/244–246
See application file for complete search history.

(56) References Cited

U.S. PATENT DOCUMENTS

| | | | |
|---|---|---|---|
| 2,694,335 A | | 11/1954 | Clayton, Jr. |
| 2,824,968 A | * | 2/1958 | Sparks, Jr. et al. ............ 250/429 |
| 4,181,437 A | * | 1/1980 | Rossiter ........................ 356/246 |
| 4,822,166 A | | 4/1989 | Rossiter et al. |
| 6,104,485 A | | 8/2000 | Wang et al. |
| 6,521,127 B1 | | 2/2003 | Chancellor |

FOREIGN PATENT DOCUMENTS

| | | |
|---|---|---|
| EP | 0 222 465 | 5/1987 |
| EP | 0 332 732 | 9/1989 |
| JP | 2-176454 | 7/1990 |
| WO | 93/17324 | 9/1993 |

OTHER PUBLICATIONS

Brown et al., "Novel Sampling Device for Obtaining Process Near-Infrared Spectra of High-Pressure Gases", *Applied Spectroscopy*, vol. 52, No. 5, May 1998, pp. 746-749, XP000776224.
Weyer, "Near-Infrared Spectroscopy of Organic Substances", *Applied Spectroscopy*, vol. 21, No. 1/2, 1985, pp. 1-43, XP002140635.
International Search Report for PCT/GB2006/004295 mailed Feb. 14, 2007.
Written Opinion for PCT/GB2006/004295 mailed Feb. 14, 2007.

* cited by examiner

*Primary Examiner* — Michael P Stafira
(74) *Attorney, Agent, or Firm* — Nixon & Vanderhye (57) ABSTRACT

Apparatus for obtaining the gas-phase electromagnetic radiation spectrum of a liquid sample, including an analysis chamber having an inlet and an outlet, wherein the inlet and analysis chamber are such that, in use, liquid sample is drawn into the inlet through capillary action and vaporized therein. The vaporized liquid sample is maintained in the gas-phase within the inlet and the analysis chamber.

31 Claims, 6 Drawing Sheets

METHOD AND APPARATUS FOR SPECTROSCOPIC ANALYSIS

This application is the U.S. national phase of International Application No. PCT/GB2006/004295 filed 17 Nov. 2006 which designated the U.S. and claims priority to European Patent Application No. 05257186.6 filed 22 Nov. 2005, the entire contents of each of which are hereby incorporated by reference.

The present invention relates to the field of spectroscopy, more specifically to obtaining a gas-phase spectrum of a liquid-phase sample.

BACKGROUND OF THE INVENTION

In petrochemical and refinery processes, knowledge of the composition of process streams is required when evaluating, for example, product purity or the efficiency of operation of a particular part of a process, such as a reactor or a distillation column. Compositional information may be obtained on-line, wherein a sample of the contents of a process stream or vessel, for example, is analysed without the need for any manual handling and transfer of the sample from the process to a remotely located laboratory. On-line analysis can therefore reduce the time required to obtain the desired information, while also reducing the chances of sample contamination which may occur when the sample is taken and transferred to the point of analysis. Known on-line techniques for obtaining compositional information of a process stream are exemplified by on-line gas chromatography, and near infrared (NIR) spectroscopy. For example, U.S. Pat. No. 6,820,013 describes the use of NIR spectroscopy to quantify the concentrations of the components in a mixture of solvents; EP-A-0 859 236 describes the use of NIR spectroscopy to obtain compositional information of crude oil being fed to a crude distillation column, and US 2002/0067481 describes a transmission cell that may be attached directly to a conduit for spectroscopically analysing the contents.

NIR spectroscopic measurements may be performed on substances in either the liquid or the gas phase. However, NIR spectra of liquids comprising strongly interacting components, particularly components that interact through hydrogen bonding, can suffer from poor resolution due to broadening of the NIR absorption bands, which can limit the accuracy of any parameters calculated therefrom.

An on-line mass-spectrometer has been previously described in *The Analyst*, 1998, vol 123, pp 343-348, wherein the vapourisation of a liquid sample for feeding to a mass spectrometer using a heated capillary tube and a feed of helium carrier gas is described. Additionally, RU 336563 describes an apparatus for creating micro-concentrations of vapourised liquids in a carrier gas by means of a liquid-filled capillary tube fitted with a wick.

There remains a need for an improved means of obtaining an on-line gas-phase NIR spectrum of a liquid sample which avoids the need for a separate carrier gas supply.

DESCRIPTION OF THE INVENTION

According to a first aspect of the present invention, there is provided an apparatus for obtaining the gas-phase electromagnetic radiation spectrum of a liquid sample, which apparatus comprises an analysis chamber having an inlet and an outlet, characterised by the inlet and analysis chamber being adapted such that, in use, liquid sample is drawn into the inlet through capillary action and vapourised therein, the vapourised liquid sample being maintained in the gas-phase within the inlet and the analysis chamber.

An advantage of the present invention is that a gas-phase electromagnetic spectrum of a liquid sample may be obtained, for example an infrared, ultraviolet/visible or NIR spectrum. In a preferred embodiment, the apparatus of the present invention is suitable for the collection of a gas-phase NIR spectrum of a vapourised liquid sample, which enables improved spectral resolution to be achieved compared to the corresponding liquid-phase NIR spectrum, particularly for liquids comprising two or more strongly interacting components. As compositional information may be obtained from a NIR spectrum, the improved resolution of the gas-phase spectrum can enable lower concentrations of components within the liquid sample to be more accurately determined. Furthermore, obtaining the spectrum of a vapourised liquid sample is preferable to obtaining the corresponding spectrum of vapour in the vapour-space above a liquid sample, as the vapour-space composition will not necessarily be representative of the composition of the liquid from which it derives. A further advantage of the present invention is that there is no requirement to use a carrier gas in order to ensure vapourisation of the liquid sample or to carry the vapourised liquid sample through the apparatus. Yet another advantage of the present invention is that no moving parts, such as from a pump, are required in order to transfer liquid sample into the inlet and to vapourise the liquid sample.

The apparatus of the present invention comprises an analysis chamber having an inlet and an outlet. The analysis chamber and the inlet are adapted such that, in use, the liquid sample is vapourised in the inlet, and maintained in the gas-phase within the inlet and analysis chamber. At least a portion of the inlet is adapted so that, in use, liquid sample is drawn into the inlet through capillary action. In a preferred embodiment, this is achieved by means of a porous mass, the surface area of which porous mass is greater than the surface area of the inner walls of the portion of the inlet in which it is contained. Thus, when in use, liquid sample is drawn into the inlet by capillary action through pores or channels of the porous mass, the high surface area of the porous mass allowing efficient vapourisation of the liquid sample. A further advantage of the porous mass is that it can also act as a filter, preventing solid particles from entering the inlet and analysis chamber which could otherwise negatively affect the NIR spectrum.

The porous mass is capable of drawing the liquid sample into the inlet through capillary action. The porous mass is also preferably capable of withstanding temperatures that are in excess of the vapourisation temperature of the liquid sample. Additionally, it is preferable that the porous mass does not degrade or deteriorate in use as a result of reaction with components of the liquid sample.

The porous mass may be selected, for example, from one or more of the group comprising a bundle of parallel tubes or rods, packed spheres or granules, one or more fibrous materials, a mesh, or a porous block such as a monolith. Preferably, the porous mass comprises beads or fibres of silica or glass, steel mesh, ceramic wool or paper. More preferably, the porous mass comprises silica fibres, which are generally highly chemically and thermally stable and are effective at absorbing polar liquids through capillary action over extended periods of time. In one embodiment of the present invention, the analysis chamber comprises more than one inlet, each adapted as hitherto described.

Both the inlet and the analysis chamber preferably have a heater in order to vapourise the liquid sample and maintain the vapourised liquid sample in the gas-phase. The heater may be a single heater that is shared by both the inlet and analysis chamber, or the inlet and analysis chamber may each have separate heaters. The heaters are capable of heating the inlet and analysis chamber to a temperature at or above the vapourisation temperature of the liquid sample. In one embodiment of the invention, the analysis chamber is heated by an electrical trace heating means, while the inlet is surrounded by a heatable metal block.

Electromagnetic radiation can enter and leave the analysis chamber. The analysis chamber preferably has windows that are transparent, or at least partially transparent, to the frequencies of electromagnetic radiation that are used for obtaining the electromagnetic radiation spectrum. In a preferred embodiment of the invention, in which the apparatus is suitable for collecting a NIR spectrum, the analysis chamber has one or more windows made of a NIR transparent material such as quartz or sapphire. Sapphire is preferred due to its strength and scratch resistance. The NIR transparent window is preferably inert to the vaporised liquid sample at the temperature of operation. In one embodiment of the invention, the analysis chamber is cylindrical, with an NIR transparent window at each face.

The outlet may optionally have a heater, which can either be controlled independently from or together with the heater(s) of the inlet and/or analysis chamber. Preferably, the temperature of the outlet is lower than that of the analysis chamber, which facilitates the maintenance of a flow of vaporised liquid sample from the analysis chamber into the outlet due to cooling of the vaporised liquid sample in the outlet. More preferably, the outlet is unheated, which can enable condensation of the vaporised liquid to occur within the outlet when the apparatus is in use, which further assists in maintaining a flow of vaporised liquid from the analysis chamber into the outlet. The apparatus of the present invention may have more than one outlet.

The inlet, outlet and analysis chamber are preferably made of materials that are inert to the liquid sample at the temperature of operation. Suitable materials include, for example, stainless steel, zirconium, titanium or Hastelloy™.

The inlet is capable of being attached to a conduit or vessel containing a liquid sample, such as a storage tank or a transfer line. Preferably, the outlet is also capable of being connected to the same conduit or vessel, so that the liquid sample entering the apparatus is returned to the conduit or vessel, thus avoiding wastage of material. The apparatus optionally has valves to allow its isolation from the process conduit or vessel to which it may be attached.

In a preferred embodiment of the present invention, the apparatus additionally comprises an inlet for a pressurising gas, preferably an inert gas such as nitrogen, argon or helium. This can reduce the possibility of a back-flow of liquid from the outlet into the analysis chamber when the apparatus is in use.

The apparatus of the present invention may be used in a process for the collection of a gas-phase electromagnetic radiation spectrum of a liquid sample. Thus, according to a second aspect of the present invention, there is provided a method for obtaining the gas-phase electromagnetic radiation spectrum of a liquid sample, comprising the steps of;

(a) feeding a liquid sample to the inlet of an apparatus comprising an analysis chamber having an inlet and an outlet, in which the liquid sample is drawn into the inlet through capillary action and vapourised therein, which vapourised liquid sample passes into the analysis chamber;

(b) directing one or more frequencies of electromagnetic radiation into the analysis chamber;

(c) detecting one or more frequencies of electromagnetic radiation transmitted through and/or emitted by the vapourised liquid sample in the analysis chamber by a detector;

(d) passing the vapourised liquid sample from the analysis chamber to the sample outlet;

(e) calculating the absorption characteristics of the vapourised liquid sample from the one or more frequencies of electromagnetic radiation received by the detector in step (c).

The process of the present invention preferably employs an apparatus as hereinbefore described. The inlet of the apparatus is connected to a source of the liquid sample to be analysed, such as a process conduit or vessel containing the liquid sample. Optionally and preferably, the outlet is also connected to the source of liquid sample to reduce the necessity for disposal of the analysed liquid sample. Optionally, the apparatus has valves to isolate it from the source of liquid sample when not in use.

In order to vapourise and maintain the liquid sample in the gas-phase, the inlet and analysis chamber are both maintained at a temperature at or above the vapourisation temperature of the liquid sample, and above the dew point of the vapourised liquid sample. This is preferably achieved by heating the inlet and analysis chamber. Although they may both be heated using a single, shared heater, optionally the inlet and analysis chamber are heated independently by separately controlled heaters. Suitably, the analysis chamber and inlet are each maintained at a temperature in the range from 50 to 600° C., preferably from 100 to 300°.

The process may operate at atmospheric pressure, higher than atmospheric pressure, or lower than atmospheric pressure depending on the nature of the liquid sample or the conditions in the conduit or vessel in which the liquid sample is contained prior to the spectroscopic analysis. In one embodiment of the present invention, the apparatus is maintained at a higher pressure than the source of liquid sample, which reduces the chance of a back-flow of liquid sample from the outlet into the analysis chamber of the apparatus.

The liquid sample enters the inlet through capillary action, wherein it is vapourised. The vapourised liquid sample passes into the analysis chamber, into which one or more frequencies of electromagnetic radiation are directed. On entering the analysis chamber, the electromagnetic radiation directed therein interacts with the vapourised liquid sample, and emitted and/or transmitted electromagnetic radiation leaves the analysis chamber and is detected by a detector.

The absorption characteristics of the vapourised liquid sample at the one or more frequencies of electromagnetic radiation detected by the detector are calculated. This is typically carried out by a spectrometer. Dispersive or interferometric techniques may be used to collect an electromagnetic spectrum. Interferometry techniques, such as Fourier Transform spectroscopy or Fabrey-Perot interferometry, are preferred, as spectra are generally quicker to obtain and have improved signal to noise ratios.

In a preferred embodiment of the process of the present invention, the one or more frequencies of electromagnetic radiation are in the near infrared (NIR) range, typically from 4000 $cm^{-1}$ to 10000 $cm^{-1}$. Resolutions of less than 16 $cm^{-1}$, for example 8 $cm^{-1}$ or below, or 4 $cm^{-1}$ or below are preferred as use can be made of rotational fine structure that occurs in this region of the spectrum and which typically have narrow peak widths. This improves accuracy and detection limits of component-concentrations calculated from the spectra. In a preferred embodiment of the present invention the resolution is 2 $cm^{-1}$ or below.

Use of NIR radiation is advantageous as it can be transmitted through optical fibres, allowing the NIR source and detector to be situated remotely from the rest of the apparatus. NIR spectra are also of use in that they may be used to obtain quantitatively the composition of the vapourised liquid sample. Concentrations of components in the vapourised liquid sample may be determined, for example, by comparison of the relevant peak areas of the NIR spectrum, or by comparing the NIR spectrum with a database of known standards using a computer programmed to perform multivariate statistical analysis techniques, such as partial least squares regression.

Detection limits of components within the liquid sample are generally improved by increasing the signal to noise ratio of the obtained NIR spectrum. Thus, increasing the number of scans over which an averaged spectrum may be obtained will generally increase the signal to noise ratio, and may also assist in improving spectral resolution. In one embodiment of the invention, a tuneable diode laser is used to continuously scan across a single peak of the spectrum from which a component concentration may be obtained, which narrows the width of the spectrum required, and reduces scan time.

The vapourised liquid sample enters the outlet from the analysis chamber. The outlet is optionally heated. Preferably, the outlet is maintained at a temperature lower than that of the analysis chamber. In such an embodiment, the vapour cools as it enters the outlet, which reduces the pressure therein and facilitates a flow of vapourised liquid sample from the analysis chamber into the outlet. More preferably, the outlet is unheated, which can allow condensation of the vapourised liquid sample within the outlet, further facilitating the maintenance of a flow of vapourised liquid sample from the analysis chamber into the outlet.

Preferably, the outlet is connected to a process conduit or vessel, more preferably the same process conduit or vessel that is connected to the inlet of the apparatus, in order to reduce loss or wastage of the analysed liquid sample.

The liquid sample of the present invention may be a liquid-phase sample taken from a process stream or a storage vessel of a chemicals or refinery process. The process of the present invention is particularly useful for liquid samples comprising components that strongly interact with each other, such as through hydrogen bonding. Preferably, the liquid sample comprises water. Yet more preferably, the liquid sample comprises water and a carboxylic acid, most preferably water and acetic acid.

The process of the present invention may be used to determine accurately low concentrations of one strongly interacting component in a liquid sample which predominantly comprises one other component with which it strongly interacts. Preferably, the low concentration component is water. Even more preferably, the liquid sample comprises predominantly acetic acid containing a low concentration of water, such as less than 1 wt % water.

The frequencies of electromagnetic radiation used will be dependent on the components of the liquid sample. A preferred frequency range for an acetic acid/water mixture, for example, would be from 7500 to 5000 $cm^{-1}$.

BRIEF DESCRIPTION OF THE DRAWINGS

The invention will now be illustrated by the following non-limiting example, with reference to the figures, in which.

DETAILED DESCRIPTION OF PREFERRED EMBODIMENTS

Figure 1:
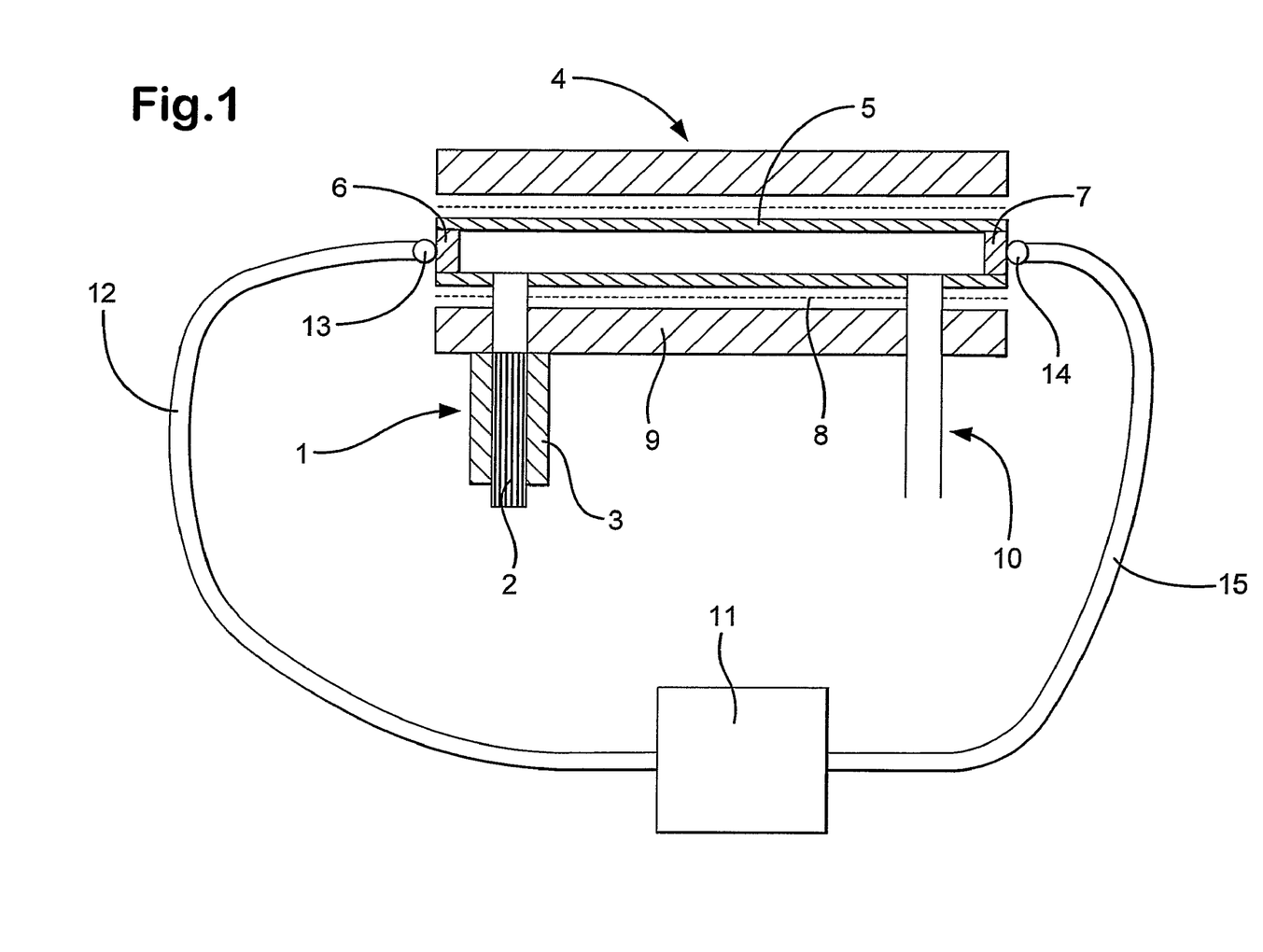
FIG. 1 is a schematic view of an apparatus according to the present invention.

An apparatus according to the present invention is shown in FIG. 1. Inlet 1 comprises a 12 mm diameter and 12.7 cm long section of stainless steel pipe and a bundle of silica fibres 2. Surrounding the inlet is an aluminium block 3 that can be heated. The analysis chamber 4 consists of a 20 cm long stainless steel pipe 5 fitted at either end with sapphire windows 6 and 7. The analysis chamber is surrounded by trace heating elements 8 and has a surrounding layer of ceramic wool lagging 9. Thermocouples (not shown) are used to measure the temperatures at the bundle of glass fibres and analysis chamber respectively, and to control the respective heating devices. The outlet 10 is unlagged and unheated. NIR radiation, emitted from a photodiode in spectrometer 11, is transferred via fibre optic cable 12 to the analysis chamber 4 through collimating lens 13 and sapphire window 6. Transmitted NIR radiation leaves the analysis chamber through sapphire window 7, and is transferred to an NIR detector in spectrometer 11 through fibre optic cable 15 via collimating lens 14.

Figure 2:
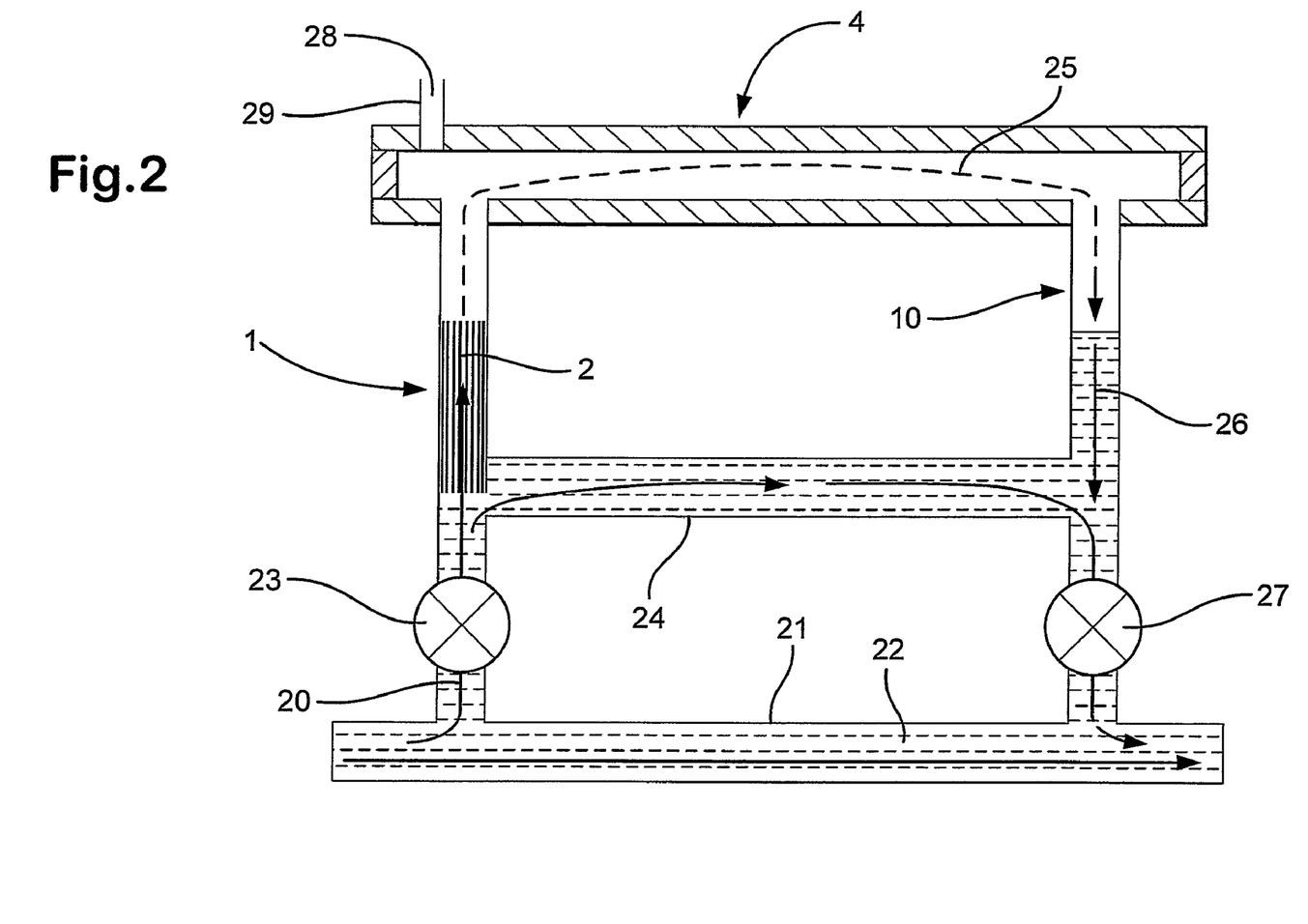
FIG. 2 is a schematic view of the path taken by the liquid sample and vapourised liquid sample in a process according to the present invention through an apparatus according to the present invention.

FIG. 2 illustrates the possible paths taken by a liquid sample during a process according to the present invention using an apparatus according to the present invention. Heavy-lined arrows correspond to the paths of liquid-phase sample, and dashed arrows correspond to paths of vapourised sample. Heaters, lagging, the spectrometer and fibre optic cables and lenses have been omitted for clarity.

A liquid sample 20, taken from a conduit or vessel 21 which contains the liquid for analysis 22, flows through open valve 23 where it either contacts a bundle of glass fibres 2 in inlet 1, or proceeds through by-pass conduit 24. Liquid sample contacting the bundle of glass fibres 2 is drawn into heated inlet 1 by capillary action, wherein it is vapourised. The vapourised liquid sample 25 enters heated analysis chamber 4, wherein it is irradiated by NIR radiation (not shown). The vapourised liquid sample, still in the gas-phase, passes through the analysis chamber and into unheated and unlagged outlet 10, wherein it condenses. The condensed vapourised liquid sample 26 passes through outlet valve 27 and back into the conduit or vessel 21 from which it was originally taken. A source of pressurising gas 28 is supplied to analysis chamber 4 through inlet 29 in order to maintain the analysis chamber, inlet and outlet at a higher pressure than the liquid 22 in conduit or vessel 21.

Example

An apparatus as illustrated in FIGS. 1 and 2 was used to obtain, on-line, the water content of a purified acetic acid product stream produced by a methanol carbonylation pilot plant, based on the iridium-catalysed process described in Sunley & Watson, *Catalysis Today*, 58, 2000, pp 293-307, which process comprises a reactor, a flash separation zone, and a purification zone comprising a combined light ends/drying column and a heavy ends column. In this example, the purified acetic acid product stream extracted from the heavy ends column of the pilot plant had a flow rate of approximately 67 g/min and a pressure of 1.4 barg (240 kPa). The inlet and analysis chamber were both heated independently to 180° C. Acetic acid was drawn into the analysis chamber at a rate of from 0.3 to 1.0 g/min, resulting in a flow rate of vapourised acetic acid at a rate of from 0.2 to 0.7 cm/s. Nitrogen was used as the pressurising gas.

NIR radiation with a frequency of from 10000 $cm^{-1}$ to 4000 $cm^{-1}$ was produced by a quartz halogen lamp from a Bomen MB 160 FTIR spectrometer, which was also equipped with a thermoelectric cooled InAs detector. Silica fibre optic cables were used to direct NIR radiation to and from the analysis chamber. Data were collected at a resolution of 2 $cm^{-1}$. A personal computer was used to calculate the water concentration of the vapourised sample by comparison of the NIR spectrum with a database of known standards using partial least squares regression analysis.

Figure 3A:
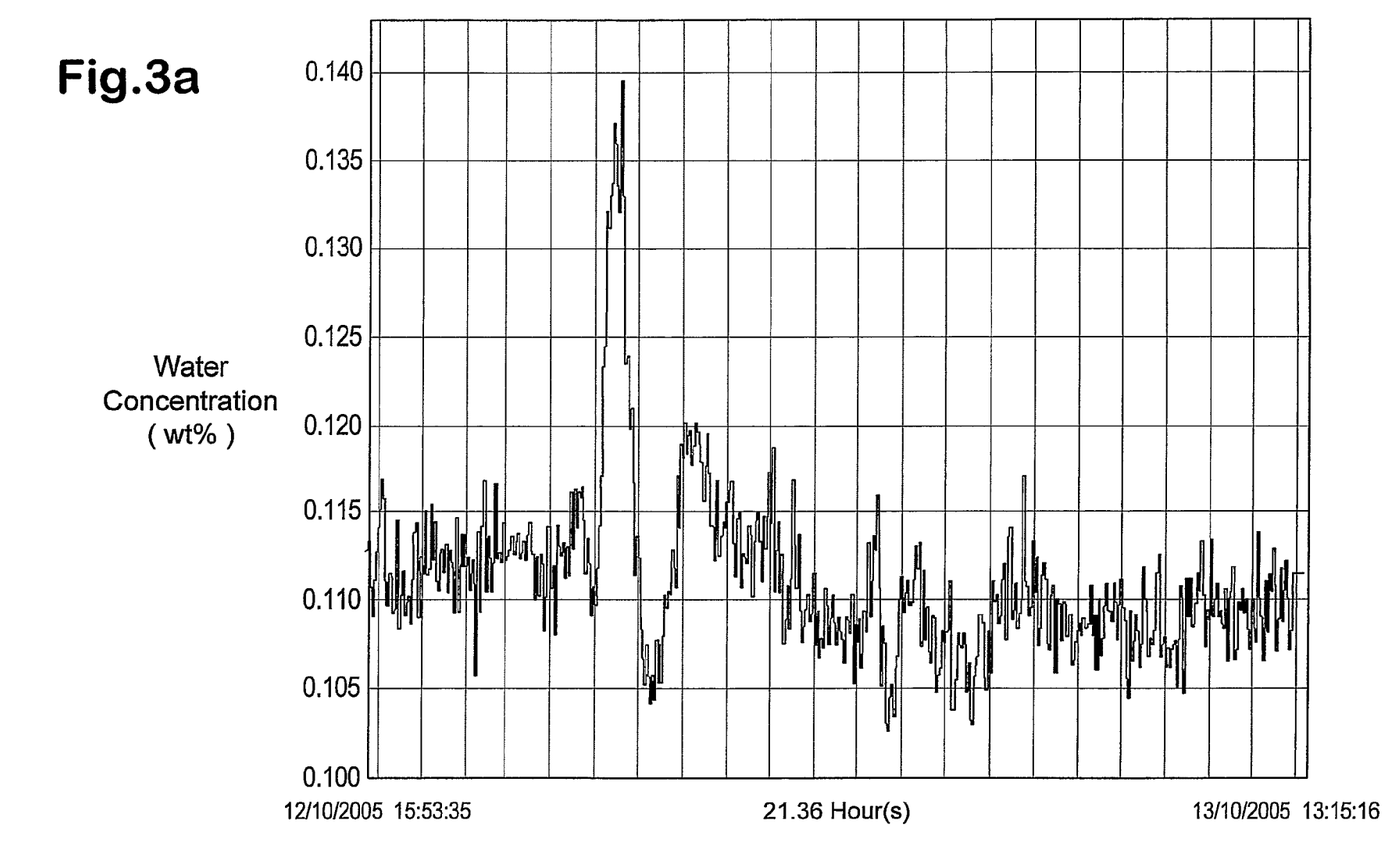
FIGS. 3a and 3b are graphs of water content of a purified acetic acid product stream versus time as obtained by a process according to the present invention with an apparatus according to the present invention.
Figure 3B:
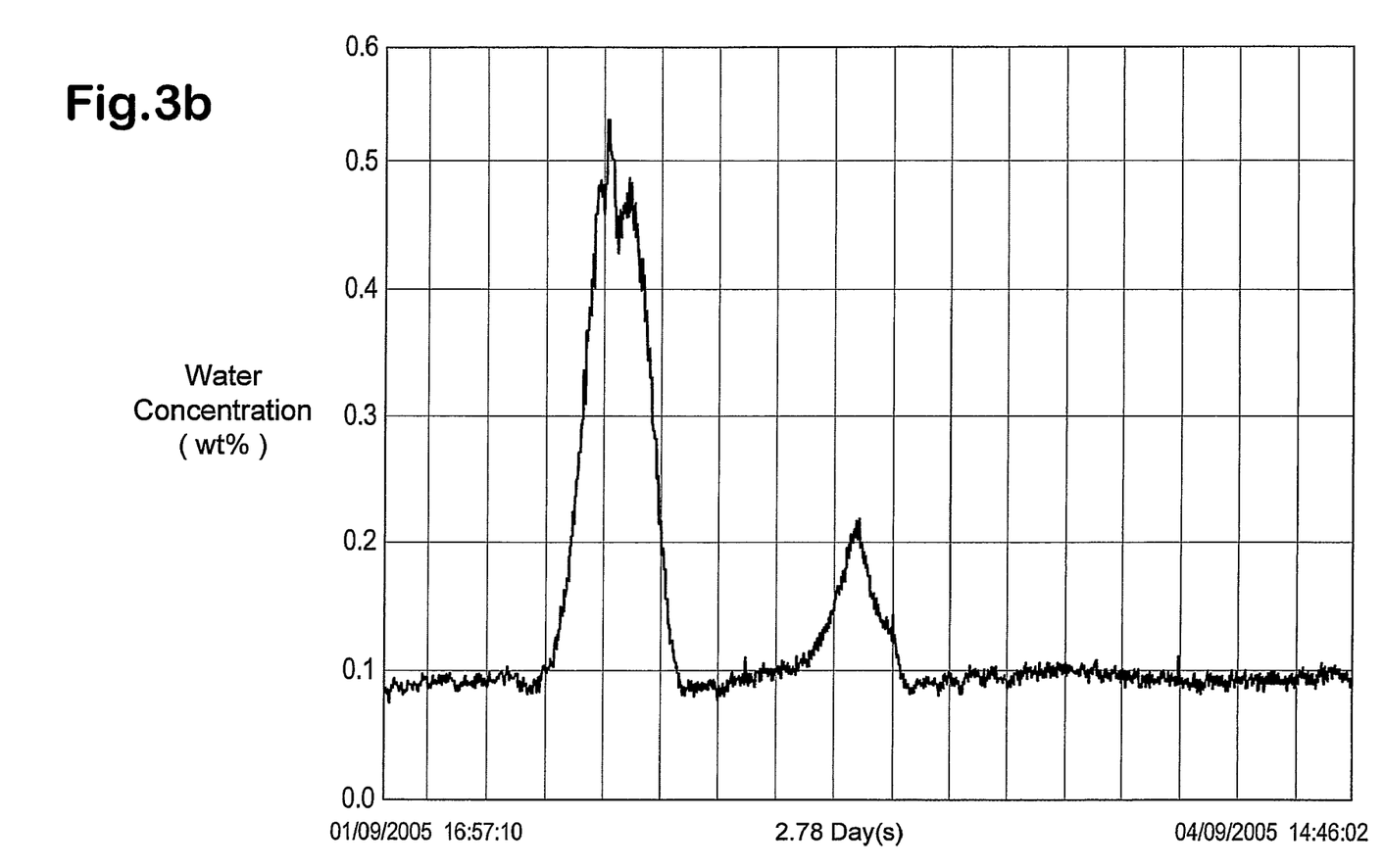
Figure 4A:
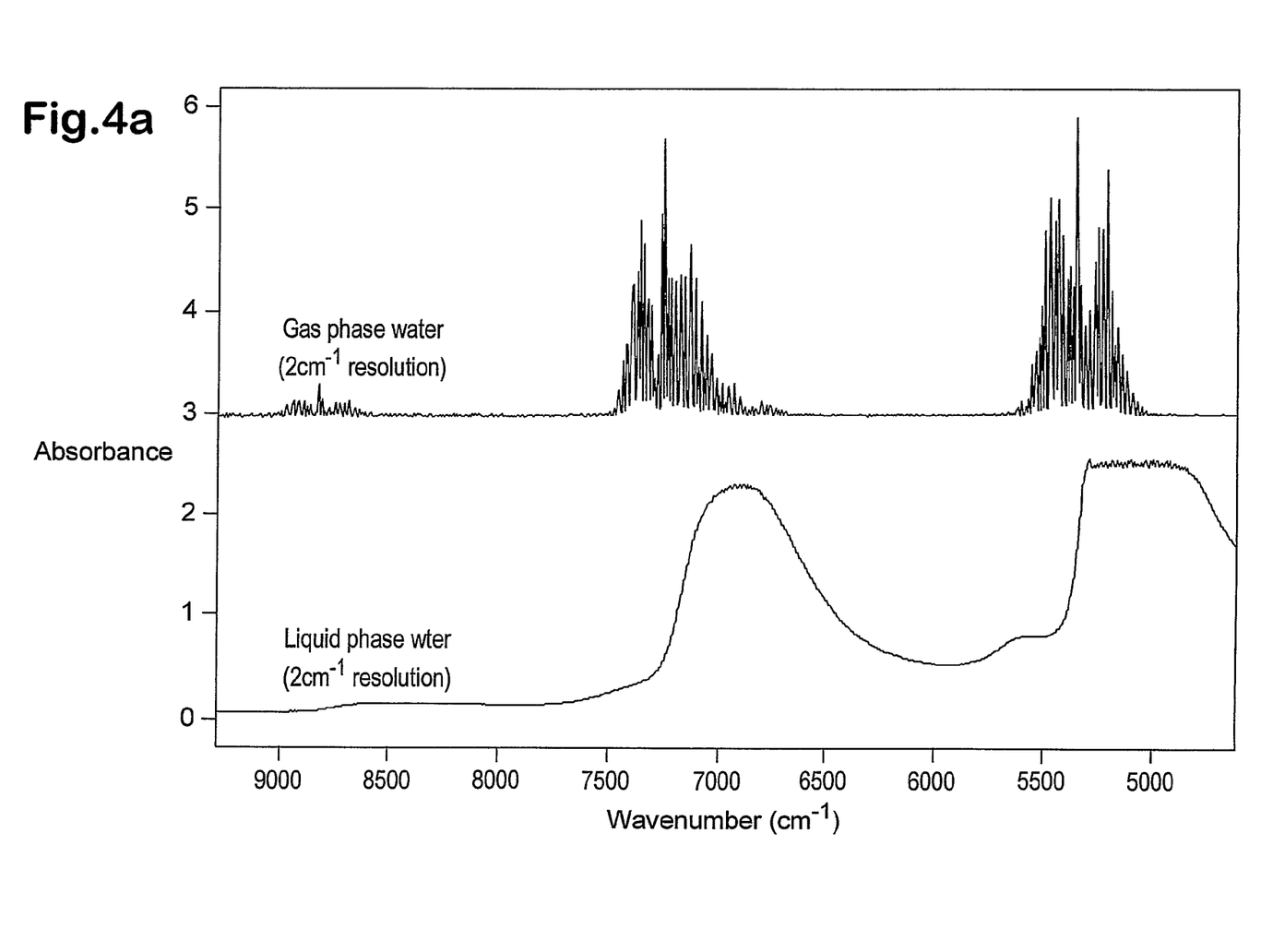
FIGS. 4a and 4b are NIR spectra of water and acetic acid respectively in the gas-phase and liquid-phase, in which the corresponding gas- and liquid-phase spectra have been collected at the same spectral resolution.
Figure 4B:
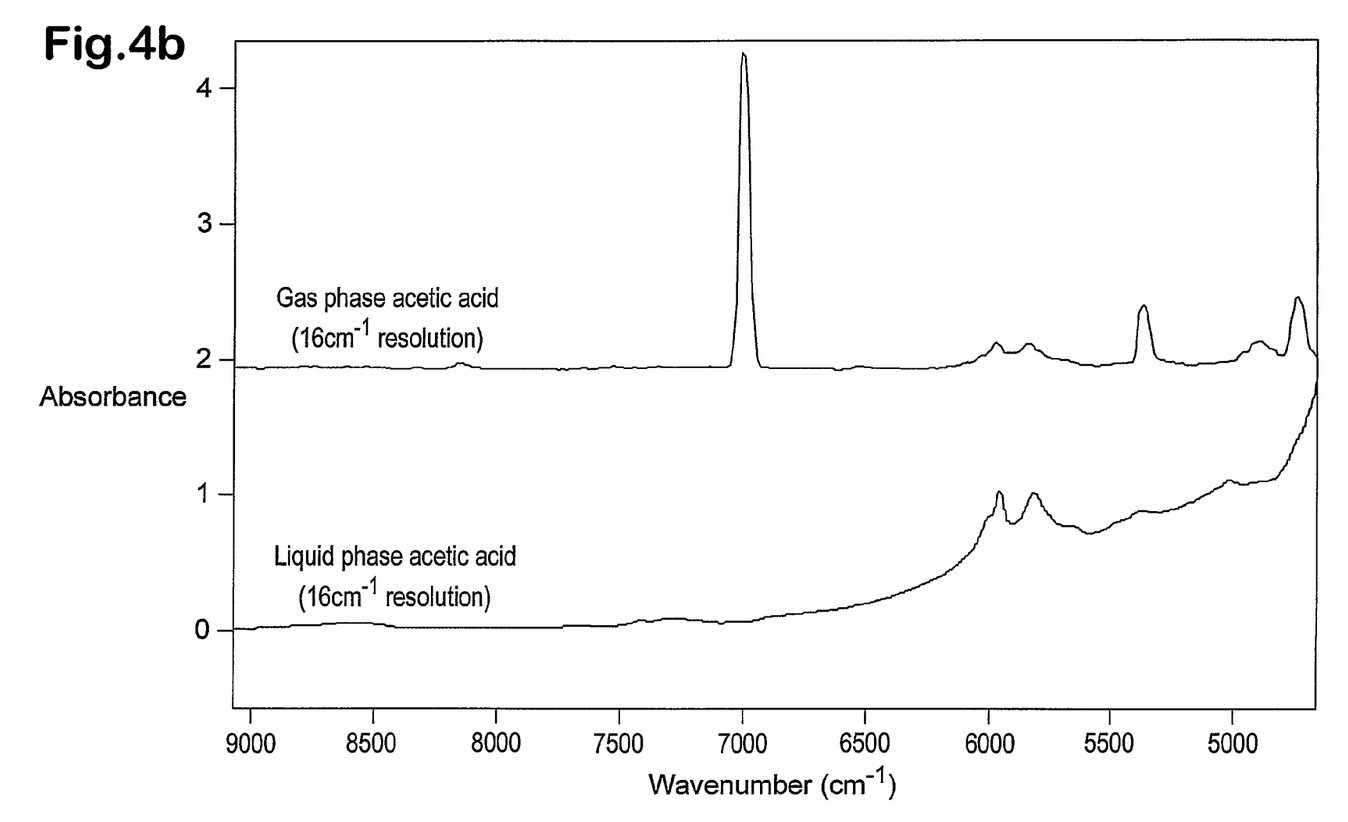

The water content of the acetic acid product stream was monitored over a period of about 67 hours. A plot of the water content (in wt %) versus time calculated from the NIR spectra are shown in FIGS. 3a and 3b. From FIG. 3a, it can be seen that the precision of the measurements is approximately ±25 ppm, corresponding to a minimum detection limit of approximately 100 ppm. This is lower than the limit obtainable from a corresponding liquid-phase NIR spectrum, which is about 1000 ppm, and results from improved peak intensities and resolution of gas-phase NIR spectra compared to corresponding liquid-phase spectra, as shown in FIGS. 4a and 4b for water and acetic acid respectively.

The invention claimed is:

1. An apparatus for obtaining the gas-phase electromagnetic radiation spectrum of a liquid sample, which apparatus comprises an analysis chamber having an inlet and an outlet, wherein the inlet and analysis chamber are such that, in use, liquid sample is drawn into the inlet through capillary action and vapourised therein, the vapourised liquid sample being maintained in the gas-phase within the inlet and the analysis chamber.

2. An apparatus as claimed in claim 1, in which at least a portion of the inlet contains a porous mass having a surface area greater than the surface area of the inner walls of the portion of the inlet in which it is contained.

3. An apparatus as claimed in claim 2, in which the porous mass comprises one or more of the group comprising a bundle of parallel tubes or rods, packed spheres or granules, one or more fibrous materials, a mesh, or a porous block.

4. An apparatus as claimed in claim 3, in which the porous mass comprises one or more of the group comprising fibres of silica or glass, steel mesh, ceramic wool or paper.

5. An apparatus as claimed in claim 4, in which the porous mass comprises silica fibres.

6. An apparatus as claimed in claim 1, in which the inlet and analysis chamber are heated.

7. An apparatus as claimed in claim 1, in which the outlet is unheated.

8. An apparatus as claimed in claim 1, in which the electromagnetic radiation is near infrared radiation.

9. An apparatus as claimed in claim 1, in which the analysis chamber comprises one or more windows that are transparent to the frequencies of electromagnetic radiation that are used for obtaining the electromagnetic radiation spectrum.

10. An apparatus as claimed in claim 9, in which the windows of the analysis chamber are made of sapphire or quartz.

11. An apparatus as claimed in claim 10, in which the windows of the analysis chamber are made of sapphire.

12. An apparatus as claimed in claim 1, which additionally comprises an inlet for a pressurising gas.

13. A method for obtaining the gas-phase electromagnetic radiation spectrum of a liquid sample, comprising the steps of:
  (a) feeding a liquid sample to the inlet of an apparatus comprising an analysis chamber having an inlet and an outlet, in which the liquid sample is drawn into the inlet through capillary action and vapourised therein, which vapourised liquid sample passes into the analysis chamber;
  (b) directing one or more frequencies of electromagnetic radiation into the analysis chamber;
  (c) detecting one or more frequencies of electromagnetic radiation transmitted through and/or emitted by the vapourised liquid sample in the analysis chamber by a detector;
  (d) passing the vapourised liquid sample from the analysis chamber to the sample outlet;
  (e) calculating the absorption characteristics of the vapourised liquid sample from the one or more frequencies of electromagnetic radiation received by the detector in step (c).

14. A method as claimed in claim 13, in which at least a portion of the inlet contains a porous mass having a surface area greater than the surface area of the inner walls of the portion of the inlet in which it is contained.

15. A method as claimed in claim 14, in which the porous mass comprises one or more of the group comprising a bundle of parallel tubes or rods, packed spheres or granules, one or more fibrous materials, a mesh, or a porous block.

16. A method as claimed in claim 15, in which the porous mass comprises one or more of the group comprising fibres of silica or glass, steel mesh, ceramic wool or paper.

17. A method as claimed in claim 16, in which the porous mass comprises silica fibres.

18. A method as claimed in claim 13, in which the inlet and analysis chamber are heated.

19. A method as claimed in claim 18, in which the inlet and analysis chamber are each heated to a temperature of from 100 to 300° C.

20. A method as claimed in claim 13, in which the outlet is unheated.

21. A method as claimed in claim 13, in which the analysis chamber comprises one or more windows that are transparent to the frequencies of electromagnetic radiation that are used for obtaining the electromagnetic radiation spectrum.

22. A method as claimed in claim 21, in which the windows of the analysis chamber are made of sapphire or quartz.

23. A method as claimed in claim 22, in which the windows of the analysis chamber are made of sapphire.

24. A method as claimed in claim 13, in which the electromagnetic radiation is near-infrared radiation.

25. A method as claimed in claim 13, in which the apparatus is attached to a process conduit or vessel which contains the liquid sample.

26. A method as claimed in claim 13, in which the liquid sample comprises components that interact through hydrogen bonding.

27. A method as claimed in claim 26, in which the liquid sample comprises predominantly acetic acid containing less than 1 wt % of water.

28. A method as claimed in claim 24, in which the near-infrared spectrum is obtained using Fourier Transform spectroscopy or Fabrey-Perot interferometry.

29. A method as claimed in claim 13, in which an inert gas is fed to the apparatus at a pressure sufficient to prevent backflow from the outlet into the analysis chamber.

30. An apparatus as claimed in claim 3, in which the porous block is a monolith.

31. An apparatus as claimed in claim 15, in which the porous block is a monolith.

* * * * *